(12) United States Patent
Batdorf

(10) Patent No.: US 6,884,741 B2
(45) Date of Patent: Apr. 26, 2005

(54) ANTIMICROBIAL SHEETING ARTICLE

(75) Inventor: Vernon H. Batdorf, Minneapolis, MN (US)

(73) Assignee: H.B. Fuller Licensing & Financing, Inc., St. Paul, MN (US)

( * ) Notice: Subject to any disclaimer, the term of this patent is extended or adjusted under 35 U.S.C. 154(b) by 190 days.

(21) Appl. No.: 10/202,270

(22) Filed: Jul. 23, 2002

(65) Prior Publication Data

US 2004/0043686 A1 Mar. 4, 2004

(51) Int. Cl.$^7$ .......................... B32B 27/12; B32B 27/04
(52) U.S. Cl. ...................... 442/123; 442/124; 442/164; 442/180; 428/41.8; 428/352
(58) Field of Search ................. 442/123, 124, 442/164, 180; 428/41.8, 352

(56) References Cited

U.S. PATENT DOCUMENTS

| | | | |
|---|---|---|---|
| 3,615,745 A | | 10/1971 | Crovetti et al. |
| 3,705,938 A | | 12/1972 | Hyman et al. |
| 3,998,944 A | | 12/1976 | Long |
| 4,246,311 A | | 1/1981 | Hirst |
| 4,629,645 A | | 12/1986 | Inoue |
| 4,808,466 A | | 2/1989 | Kotani et al. |
| 5,209,930 A | * | 5/1993 | Bowers-Daines et al. ... 424/401 |
| 5,314,719 A | | 5/1994 | Batdorf et al. |
| 5,744,239 A | * | 4/1998 | Buccellato et al. ...... 428/411.1 |
| 5,938,825 A | * | 8/1999 | Gaglani et al. ......... 106/18.32 |
| 6,106,741 A | * | 8/2000 | Heimann et al. ........ 252/389.3 |
| 6,299,520 B1 | | 10/2001 | Cheyne |
| 6,342,556 B1 | * | 1/2002 | Batdorf et al. ............. 524/432 |
| 2003/0003126 A1 | * | 1/2003 | Mount et al. ............... 424/409 |
| 2003/0096545 A1 | * | 5/2003 | Payne ....................... 442/123 |

FOREIGN PATENT DOCUMENTS

| | | |
|---|---|---|
| EP | 0 257 415 | 3/1988 |
| EP | 0 787 851 | 8/1997 |
| EP | 0 937 812 A2 | 8/1999 |
| GB | 2 095 297 A | 9/1982 |
| WO | WO 99/59410 | 11/1999 |
| WO | WO 01/58261 | 8/2001 |

OTHER PUBLICATIONS

Database WPI, Section Ch. Week 199934, Derwent Publications Ltd., London, GB; AN 1999–400085, XP002259923 & JP 11 158017 A (Mitsubishi Paper Mills Ltd.), Jun. 15, 1999, abstract.
Database WPI, Section Ch. Week 199749, Derwent Publications Ltd., London, GB; AN 1997–532932, XP002259924 & JP 09 255898 A (Kyodo Printing Co. Ltd.), Sep. 30, 1997, abstract.
Database WPI, Section Ch. Week 199351, Derwent Publications Ltd. London, GB; AN 1993–410530, XP002259925 & JP 05 309795 A (Mitsubishi Rayon Co. Ltd.), Nov. 22, 1993, abstract.
Database WPI, Section Ch. Week 1985544, Derwent Publications Ltd., London, GB; AN 1985–273477, XP002259926 & JP 60 185872 A (Sumitomo Naugatuck KK), Sep. 21, 1985, abstract.
Database WPI, Section Ch. Week 198806, Derwent Publications Ltd., London, GB; AN 1988–040159, XP002259927 & JP 62 299578 A (Washi Chuetsu Board), Dec. 26, 1987, abstract.

* cited by examiner

*Primary Examiner*—Ula Ruddock
(74) *Attorney, Agent, or Firm*—Bin Su

(57) ABSTRACT

The invention relates to an antimicrobial article in a sheet form including a porous sheeting substrate impregnated with a water-based antimicrobial composition comprising at least one polymeric emulsion or dispersion and at least one antimicrobial component that is substantially non-leaching and free of environmental hazardous material. The antimicrobial article may further comprise an adhesive coating disposed on at least one surface of the antimicrobial article. A removable protective film may be held to the exposed surface of the adhesive coating. The invention also provides a process of manufacturing the antimicrobial article. The antimicrobial article can be used, e.g., over fiberglass pipe insulation, on air duct liners, in building wall cavities, over gypsum wallboard and other construction surfaces.

27 Claims, No Drawings

US 6,884,741 B2

ANTIMICROBIAL SHEETING ARTICLE

FIELD OF THE INVENTION

The invention relates to an antimicrobial article in a sheet form for constructions in industrial and commercial application. The antimicrobial article includes a porous sheeting substrate impregnated with a water-based antimicrobial composition that is substantially free of environmental hazardous materials and to a process of manufacturing the antimicrobial article.

BACKGROUND OF THE INVENTION

A widely used method of providing certain active properties, e.g., antibacterial, fungistatic or fungicidal properties, to an exposed surface of an object is to cover the exposed surface with a coating composition containing active component(s). The coating composition is applied directly on that surface and then dried on site to form an active coating on the surface. As the majority of the active coating compositions are solvent-based, hazardous volatile organic solvent(s) are evaporated during the application and drying process, which inevitably causes health problems, fire danger, and environmental pollution. Water based active coating compositions need to take a longer time to dry after application, which is less efficient and causes delay of being put into service when needed. All in all, these active coatings are normally thin coatings (e.g., 1–5 mils) that are easily damaged by e.g., abrasion, scrubbing, weathering or wear. Thus, they could only provide limited service life and efficiency to the exposed surface of the object. Further, as these coatings are typically applied thin, there is very little antimicrobial activity per unit area, with resultant lack of microbial protection in high exposure environment.

Some efforts were made to replace active coatings with certain laminates that incorporate active agent(s) to cover the surface of an object. These laminates either use environmental hazardous material(s) as active agent(s), or have various complicated multilayers. The active agents are only added to the laminates at a level so as to protect the covered object itself from microbial degradation. However, these laminates could not provide the desirable antimicrobial efficacy on their exposed surfaces due to the use of the crosslinked polymer systems or extruded thermoplastic polymers to make the laminates. The crosslinked polymer systems or the extruded thermoplastic polymers would lock the active agents in the laminates, thus, hinder the availability of the agents to act on the microbes that are settling on the exposed surfaces of the laminates.

Accordingly, it is desirable for an antimicrobial article in a sheet form that does not include environmentally hazardous material and that has excellent lasting antimicrobial properties for protecting the covered objects from degradation as well as for inhibiting the growth of all types of microorganisms on its exposed surface and being capable of killing these microorganisms. The desirable antimicrobial article in a sheet form should also be easy to make and use.

SUMMARY OF THE INVENTION

In one aspect, the invention features an antimicrobial article in a sheet form comprising a porous sheeting substrate impregnated with a water-based antimicrobial composition. The water-based antimicrobial composition comprises at least one polymeric emulsion or dispersion and at least one antimicrobial component that is substantially non-leaching and substantially free of environmentally hazardous material.

In another aspect, the invention features an antimicrobial adhesive article in a sheet form comprises a porous sheeting substrate impregnated with a water-based antimicrobial composition and a layer of an adhesive disposed on at least one surface of the impregnated sheeting substrate. The water-based antimicrobial composition comprises at least one polymeric emulsion or dispersion and at least one antimicrobial component that is substantially non-leaching and substantially free of environmentally hazardous material.

In yet another aspect, the invention provides a method of manufacturing an antimicrobial article in a sheet form comprising impregnating a porous sheeting substrate with a water based antimicrobial composition.

In yet another aspect, the invention provides a method of manufacturing an antimicrobial adhesive article in a sheet form comprising impregnating a porous sheeting substrate with a water based antimicrobial composition and applying an adhesive on at least one surface of the impregnated sheeting substrate.

The antimicrobial article of the invention can be manufactured to be substantially free of environmental hazardous material, e.g., arsenic, mercury, lead, tin, copper, and also to be substantially free of volatile organic component(s), such as, organic solvent(s) as the carrier of the components of the composition.

The antimicrobial article of the invention is designed to be moisture breathable such that the active antimicrobial component contained therein could diffuse through the absorbed moisture within the article to the surface(s) of the article as needed to kill the microorganisms thereon.

The antimicrobial article of the invention is designed to be a true antimicrobial article such that the microorganisms can be killed on its surface(s) upon direct contact, or within an inhibited zone, i.e., in close proximity, e.g., within a horizontal and/or vertical distance of about 3 mm to about 4 mm from its surface(s). The antimicrobial article can also kill the microorganisms deposited on the surface(s) of dirt, debris or other food sources that are settling on its surface(s).

The antimicrobial article of the invention provides uniform surface antimicrobial properties including zero growth of microorganisms e.g., fungi, bacteria, yeast, or algae, etc. on at least one surface(s) of the article according to the modified ASTM G-21.

The antimicrobial article of the invention also exhibits the capability of destroying insects, such as pests, e.g., termites.

The antimicrobial article of the invention also exhibits very good physical properties, e.g., stability; water and stain resistance; impact, puncture and tear resistance; high flexibility and tensile strength.

The antimicrobial article of the invention also exhibits good opacity and can be formulated for any color.

The antimicrobial article of the invention is easy to manufacture, easy to store and easy for application, e.g., it can be rolled up for storage, or it can be installed directly over fiberglass pipe or air-duct insulation, or over metal or plastic substrates, construction materials on walls, ceilings and flooring, or on furnishings.

Other features of the invention will be apparent from the following description of the invention and preferred embodiments thereof, and from the claims.

DETAILED DESCRIPTION OF THE INVENTION

The antimicrobial article of the invention comprises a porous sheeting substrate impregnated with a water based antimicrobial composition.

The porous sheeting substrate has open weave so that it can be easily saturated with the water based antimicrobial composition such that the individual fibers of the substrate material would be coated with the composition.

Useful sheeting substrate material includes, such as, non-polymeric material, e.g., various woven or non-woven fiberglass, Brattice cloth, cotton and other fabrics, heavy weight paper, light weight wire mesh, ceramic cloths, or polymeric material, such as, some synthetics, e.g., various woven or non-woven polyester, polypropylene, polyethylene, Nylon, synthetic fiber blend, etc.

The water based antimicrobial composition is substantially free of environmental hazardous materials, such as arsenic, mercury, lead, tin, copper, phosphates, or sulfates. The composition includes water as the carrier for all the components and is substantially free of volatile organic components, such as organic solvent(s) as the carrier(s) of the components of the composition.

The water based antimicrobial composition may have a Brookfield viscosity of from about 1 cps to about 100,000 cps depending on the sheeting substrate to be impregnated. In some embodiments, the water based antimicrobial composition can be formulated to have a low viscosity such that it can impregnate higher density sheeting materials such as acoustical ceiling tile, paper board, or cardboard. For example, the composition can be formulated to have a Brookfield viscosity of from about 1 cps to less than about 5,000 cps, preferably, to about 1,000 cps, and more preferably, to about 500 cps. In other embodiments, the water based antimicrobial composition can be formulated to have relatively high viscosity to impregnate more open weave sheeting materials. For example, the Brookfield viscosity of the composition may be from about 5,000 cps up to about 100,000 cps, preferably up to about 50,000 cps, more preferably up to about 30,000 cps, and most preferably up to about 15,000 cps.

The water based antimicrobial composition can be formulated to have a solids content of no less than about 10.0 wt %, such as, no less than about 20.0 wt %, or no less than about 30.0 wt %. On the other hand, the solids content of the composition can be up to about 75.0 wt %, such as up to about 55.0 wt %.

The water based antimicrobial composition can be formulated to have a pH value of up to about 11.0, such as up to about 10.0. The pH value of the composition can also be no less than about 3.0, such as no less than about 7.0.

The water based antimicrobial composition comprises at least one antimicrobial component and at least one polymeric emulsion or dispersion.

Useful antimicrobial component includes any active antimicrobial agent that is capable of inhibiting the growth of the microorganisms and/or killing microorganisms, e.g., fungi, bacteria, algae and yeast. The useful antimicrobial component also includes insecticides, pesticides and termiticides that are capable of repelling and/or killing insects, termites and other pests. Preferably, the antimicrobial component is capable of killing microorganisms and/or inhibiting the growth of the microorganisms or repelling and/or killing termites and other pests through direct contact or in close proximity. The antimicrobial component is substantially free of environmental hazardous material, e.g., arsenic, mercury, lead, tin, copper, phosphates and sulfates. The antimicrobial component is substantially non-leaching and non-volatile. That is, it has a very low volatility and very low water solubility such that it would only leach out to the extent sufficient to maintain an effective and uniform concentration throughout the exposed surface(s) of the antimicrobial article when its concentration thereon is reduced due to its action against microorganisms. In other words, the antimicrobial component is selected not to be fugitive or migrating once being incorporated into the impregnated article, but to have a very low water solubility so that it could maintain an equilibrium concentration throughout the article on its surface(s) whenever the concentration reduction occurs thereon due to the attack of the microbes. The antimicrobial component may have a water solubility of, for example, from about 0.10 PPM to about 1.0 wt %, depending on each individual antimicrobial component.

Examples of useful antimicrobial components include, such as, zinc omadine, sodium omadine, sodium borate, zinc borate, barium metaborate, calcium borate, iodo alkynyl alkyl carbamates, diiodomethyl-p-tolylsulfone, 2-4-thiazolyl-benzimidaxole, 2-n-octyl-4-isothiazolin-3-one, zinc dimethyldithiocarbamate, zinc 2-mercaptobenzothiazole, potassium n-hydroxymethyl-n-methyldithiscarbamate, sodium 2-mercaptobenzothiazole, 5-hydroxyemthoxymethyl-1-aza-3,7-dioxa-bicyclooctane, 2,3,5,6-tetra-chloro-4-pyridine, zinc 2-pyridinethiol-1-oxide, N-trichloromethylthiophthalimide, tetrachloroisophthalonitrile, deltamethrin, fipronil, bifenthrin, chlorfenapyr, imidacloprid, and mixtures thereof.

The antimicrobial component is present in the antimicrobial composition in an amount such that the antimicrobial article effectively inhibits the growth of the microorganisms and/or kills the microorganisms or repels and/or kills the termites and other pests on the exposed surface(s) of the antimicrobial article upon direct contact or in close proximity. Typically, the amount of the antimicrobial component present in the composition depends on individual active agent. For example, the antimicrobial component can be present in an amount of from about 0.080 wt % (active) to about 30.0 wt % (active), based on the total weight of the composition. For some antimicrobial components, e.g., iodo alkynyl alkyl carbamates, sodium omadine, zinc omadine, etc., a practically lower amount of about 0.080 wt % (active) and a practically higher amount of about 0.50 wt % (active) may be used. For some other antimicrobial components that are mostly of inorganic nature, e.g., zinc borate, barium borate, etc., a practically lower amount of about 2.0 wt % (active) and a practically higher amount of up to about 30.0 wt % (active), preferably up to about 20.0 wt % (active), more preferably up to about 10.0 wt % (active) may be used.

Useful polymeric emulsion or dispersion includes, e.g., an emulsion or dispersion of a film-forming polymer that has a glass transition temperature (Tg) of from about −70° F. (about −57° C.) to about 140° F. (about 60° C.). Preferably, the polymeric emulsion or dispersion has a medium particle size of from about 0.10 micron to about 4.0 micron. Examples of useful polymeric emulsion or dispersion includes, such as, emulsions or dispersions of styrene acrylic copolymers, such as Acronal S702 from BASF, PD-600 and PD-2056 F from H.B. Fuller Company, and Res 1018 and 1019 from Rohm & Haas; acrylic homopolymers, such as, PD-431, PD-449, PD-483 and PD-2049 F from H.B. Fuller Company; vinyl acrylic copolymers, such as, PD-119, and PD-124 from H.B. Fuller Company, Ucar 376 from Union Carbide, and Res 3077 from Rohm & Haas; styrene butadiene block copolymers, such as, DL 313 NA from Dow Chemical, ND-565 and ND-422 from BASF, and Rovene 6105 from Mallard Creek Polymers; ethylene vinyl acetate copolymers, such as Airflex 400/A405/460 from Air Products and Elvace 1875 from Reichhold Chemicals; polyvinyl acetate homopolymer, such as PD-316 from H.B. Fuller Company, and Airflex XX-220/230 from Air Products; acrylate-acrylonitrile copolymers, such as Synthemuls, various grades from Reichhold Chemicals; vinyl acetate-vinyl chloride ethylene copolymers, such as Airflex 728 from Air Products; ethylene vinyl acetate butyl acrylate terpolymers, such as Airflex 809 from Air Products; butadiene-acrylonitrile copolymers, such as Tylac, various grades from Reichhold Chemical; vinyl acrylic-vinyl chloride, such as Haloflex 563 from Zeneca Resins; vinylidene chloride-acrylic-vinyl chloride copolymers, such as Vycar 660X14 and Vycar 460X46 from B.F. Goodrich; chloroprene polymers and copolymers, such as DuPont Neoprene latex 115, 400, 654 and 750 from DuPont; water-borne urethane polymers, such as Neo Rez R-962, 967 and 972 from Zeneca Resins, and mixtures thereof.

The polymeric emulsion or dispersion can be present in the antimicrobial composition in an amount effective to provide various properties, such as, film forming and pigment binding properties. For example, the polymeric emulsion or dispersion can be present in an amount of from about 10.0 wt % to about 90.0 wt %, preferably from about 15.0 wt % to about 80.0 wt %, and more preferably from about 20.0 wt % to about 75.0 wt %, based on the total weight of the composition.

The water based antimicrobial composition may include other optional components. For example, zinc oxide may be incorporated as a fungistatic agent and pigment in an amount of from about 1.0 wt % to about 15.0 wt %, if desirable. Other additives typically used in polymeric emulsions or dispersions may also be incorporated, e.g., wetting agents, dispersing aids, thickeners, surfactants, pigments, defoaming agents, coalescing agents, fillers, reinforcing agents, adhesion promoters, plasticizers, flow control agents, ultraviolet (UV) absorber agents, and mixtures thereof. These additives are normally used in the art of compounding, coating, mastics, adhesives and sealants.

The antimicrobial composition of the invention may be prepared by any conventional technique using equipment typical for making coatings/paint or adhesives. A Cowles Dissolver, Hockmeyer Mixer, or even horizontal ribbon mixers are all suitable equipment, and will provide adequate dispersion.

In yet another aspect of the invention, the antimicrobial article of the invention may further comprise an adhesive layer disposed on at least one surface of the antimicrobial article to form an antimicrobial adhesive article in a sheet form. Examples of useful adhesives include, such as, pressure sensitive adhesives, heat reactive adhesives or moisture curable adhesives. In one embodiment, a pressure sensitive adhesive PD-8118 from H.B. Fuller Company is applied on one surface of the impregnated sheeting substrate. The adhesive may optionally include at least one antimicrobial component present in an amount effective to inhibit the growth of the microorganisms and/or kill the microorganisms through direct contact on the exposed surface of the adhesive layer or within the close proximity to the exposed surface of the adhesive layer.

According to the invention, the adhesive can be applied on one surface of the antimicrobial article once the article is relatively firmly set or dried. As the antimicrobial article has been saturated with the antimicrobial composition, the adhesive would form a uniform coating on the surface of the article where the adhesive is applied, but would not impregnate into the already saturated article. Having an adhesive coating disposed directly on one surface of the antimicrobial article, the antimicrobial article would be easily applied to and adhered to the exposed surface of a substrate to be protected. Preferably, the exposed surface of the substrate is reasonably clean before the application of the antimicrobial article of the invention.

Optionally, the antimicrobial adhesive article of the invention includes a removable protective film, such as a release paper held on the exposed surface of the adhesive layer to allow the article to be rolled up without adhering to itself. The protective film also protects the adhesive from being contaminated or damaged during the storage or before the application. The protective film can be easily peeled off when the antimicrobial adhesive article is to be used.

The antimicrobial article of the invention can be prepared using a variety of methods. For example, the article can be prepared by dipping a porous sheeting substrate into a pan of the water based animicrobial composition. Then, the wet impregnated sheeting substrate is squeezed between the pinch rollers on automatic equipment to remove excess coating and to force complete impregnation of all the pores. Then, it is moved through a drying zone where the wet article is dried by exposing to heat at a temperature of from about 150° F. to about 300° F., or by using infrared radiant heat. Drying time depends on the thickness and the size of the article. In some embodiments, it may take as short as about 1 minute to dry the article. In other embodiments, the article may be dried for up to about 30 minutes. The dried antimicrobial article can be rolled up on some core material for storage. In some embodiments, the sheeting substrate is saturated with the water based antimicrobial composition. In some other embodiments, the sheeting substrate is saturated and encapsulated by the antimicrobial composition such that the surface fibers on both surfaces of the sheeting substrate are substantially invisible.

The antimicrobial article can be colored to the desired color using standard pigments as used for household paints, or it could be provided in a clear color.

In the embodiment where the antimicrobial article includes a uniform layer of an adhesive on one surface of the article, the wet article may not need to be completely dried prior to the application of the adhesive. That is, the wet article may only be firmly set or partially dried. The adhesive can be applied on one surface of the antimicrobial article by any convenient means such as brush, roller coat, curtain coat, spray, extrusion, etc. Optionally, a removable protective film, e.g., a release paper is attached to the exposed adhesive film to protect the adhesive from being contaminated or damaged before the article is used or stored.

The antimicrobial article can be applied and fastened to the exposed surface of a substrate to be protected by, such as, stapling, taping, nailing, or adhering either with a pre-applied pressure sensitive adhesive, or using adhesive at the application site on the substrate to be protected. In some cases, the antimicrobial article may be free hung, as would be the case for a shower curtain.

Upon application, the antimicorbial article will be fastened over the exposed surface of the substrate to be protected to provide a new antimicrobial surface to that substrate. Thus, the exposed surface of the antimicrobial article over that substrate is functioning as an antimicrobial surface of the substrate to provide the desirable antimicrobial property to the substrate. This antimicrobial surface also has integrated physical properties, such as toughness, water resistance, low moisture permeability, desirable color and texture, which allow it functions, such as, as a moisture barrier, a decorative surface, a tough protective surface from weather, corrosion or abuse when used, e.g., over/around pipe insulation, or as an air conditioner drip pan lining or around building foundations/underground walls, in building wall cavities, under flooring/roofs, wherever antimicrobial/pesticidal properties are beneficial. Therefore, the antimicrobial surface is functioning as a finished surface and there would be no need for other coatings, e.g., powder coatings, paints, finishes, covering films, print, etc., being applied over the antimicrobial surface, or the exposed surface of the antimicrobial article.

The antimicrobial article in a sheet form can be manufactured as a rigid sheet or a flexible sheet depending on the intended use. The thickness of the antimicrobial article in sheet form may vary depending on the end use and the degree of the antimicrobial properties desired. Mainly, the specific type and thickness of the porous sheeting substrate chosen will determine the final thickness of the article. In some embodiments, the article in the sheet form may have a thickness of from about 5 mils to about 100 mils.

The antimicrobial article of the invention is ready to use and does not need spraying, rolling or brushing at the application site as conventional coatings do. Further, there is no lengthy drying time needed and no odor typical of coatings at the application site as conventional coatings do.

The antimicrobial article can be used, for example, over fiberglass pipe insulation, on air duct liners and equipment, in building wall cavities, over gypsum wall board and other construction surfaces, on shoe insoles, as a soil covering, shower curtains, rugs and mats, mattress pads, etc. The antimicrobial article can be used either interior or exterior, even used under water or in adverse weather conditions that would be detrimental to applying a typical water based coating.

The antimicrobial article is designed to be either of a temporary nature where it could be easily removed and disposed as a non-hazardous article, or of a long term nature where it could be left in place for long term antimicrobial protection.

The invention will be described further by way of the following examples. All parts, ratios, percents and amounts stated in the Examples are by weight unless otherwise specified.

EXAMPLES

Test Procedures

Test procedures used in the examples include the following.

Test Method

Antimicrobial efficacy is tested according to ASTM G21 Standard Practice for Determining Resistance of Synthetic Polymeric Materials to Fungi with the modification that potato dextrose agar is used instead of nutrient-salts agar for better growth results, and allowing for observation of any zone of inhibition.

Viscosity

Viscosity is tested at 20 RPM, 77° F. (25° C.) using a Brookfield viscometer on specimen aged in sealed container at ambient conditions for up to 12 months.

Example 1

An antimicrobial composition was prepared by combining 69.4 wt % water, 30 wt % styrene-butadiene latex (50% solids, 65% styrene), 0.20 wt % nonionic surfactant and 0.40 wt % iodo alkynyl alkylcarbamate (IPBC-40) (40% active). The resultant antimicrobial composition had a pH value of about 7 to about 8, Brookfield viscosity of about 5 to about 50 cps and a solids content of about 17.0 wt % to about 17.5 wt %.

A sheeting article was prepared by impregnating a non-woven porous Nylon sheeting material with the antimicrobial composition and drying the impregnated sheeting in an oven at about 180° F. for about 30 minutes.

The dried sheeting article was tested according to modified ASTM G 21 and the test results are listed in Table II.

Example 2

An antimicrobial composition and a sheeting article were prepared according to the procedure in Example 1 except that 0.40 wt % zinc omadine (48% active) and 1.50 wt % propylene glycol were included and that 67.5 wt % water was used instead of 69.4 wt % water.

The resultant antimicrobial composition had a pH value of about 7 to about 8, Brookfield viscosity of about 5 to about 50 cps and a solids content of about 17.0 wt % to about 17.5 wt %.

The dried sheeting article was tested according to modified ASTM G 21 and the test results are listed in Table II.

Example 3

An antimicrobial composition and a sheeting article were prepared according to the procedure in Example 1, except that the antimicrobial composition was prepared by combining 16.5 wt % water, 80 wt % styrene-acrylic latex (50% solids, Tg of 18° C.), 0.20 wt % nonionic surfactant, 0.40 wt % UV absorber, 0.30 wt % coalescing agent, 2.0 wt % zinc oxide (0.05 to 0.15 micron), 0.40 wt % IPBC-40 (40% active) and 0.20 wt % sodium omadine (40% active).

The resultant antimicrobial composition had a pH value of about 8 to about 9, Brookfield viscosity of about 800 to about 1200 cps and a solids content of about 42.0 wt % to about 42.5 wt %.

The dried sheeting article was tested according to modified ASTM G 21 and the test results are listed in Table II.

Example 4

A sheeting article was prepared by impregnating a non-woven porous Nylon sheeting material with the antimicrobial composition of Example 3 and drying the impregnated sheeting in an oven at about 180° F. for about 30 minutes.

The dried sheeting article was tested according to modified ASTM G 21 and the test results are listed in Table II.

Example 5

An antimicrobial composition and a sheeting article were prepared according to the procedure in Example 4, except that the antimicrobial composition was prepared by combining 57.65 wt % water, 33.0 wt % acrylic copolymer latex, 0.35 wt % nonionic surfactant, 0.70 wt % cellulosic thickener, 0.20 wt % UV absorber, 0.50 wt % coalescing agent, 1.50 wt % zinc oxide, 0.20 wt % silane adhesion promoter, 0.30 wt % zinc omadine, 0.30 wt % IPBC-40, 2.0 wt % plasticizer, 0.90 wt % ethylene glycol, and 2.4 wt % pigments.

The resultant antimicrobial composition had a pH value of about 8.5 to about 9.5, a Brookfield viscosity of about 2,000 to about 2,400 cps and a solids content of about 24.0 wt % to about 28.0 wt %.

The dried sheeting article was tested according to modified ASTM G 21 and the test results are listed in Table II.

Examples 6–8

Antimicrobial compositions and sheeting articles were prepared according to the procedure in Example 4, except that the antimicrobial compositions were prepared by combining ingredients listed in Table I.

The resultant compositions had a pH value of about 8.5 to about 9.0, a Brookfield viscosity of about 4,000 to about 5,000 cps and a solids content of about 54.0 wt % to about 58.0 wt %.

The dried sheeting articles were tested according to modified ASTM G 21 and the test results are listed in Table II.

TABLE I

| Ingredients (wt %) | Ex. 6 | Ex. 7 | Ex. 8 |
| --- | --- | --- | --- |
| Water | 31.5 | 31.5 | 31.5 |
| Anionic surfactant | 0.40 | 0.40 | 0.40 |
| Non-ionic surfactant | 0.60 | 0.60 | 0.60 |
| IPBC-40 | 0.30 | — | — |
| Zinc borate | 11.0 | 11.0 | — |
| Magnesium hydroxide | 23.0 | 23.0 | 23.0 |
| Zinc oxide | 2.0 | 2.0 | 2.0 |
| Cellulosic thickener | 0.30 | 0.30 | 0.30 |
| Triaryl phosphate | 3.60 | 3.60 | 3.60 |
| Vinyl acrylic latex (55% solids) | 27.0 | 27.0 | 27.0 |
| Defoamer | 0.30 | 0.30 | 0.30 |
| Barium metaborate | — | — | 11.0 |

Example 9

An antimicrobial composition was prepared by combining 64.0 wt % water, 0.80 wt % Bentonite clay, 0.20 wt % anionic surfactant, 0.40 wt % nonionic surfactant, 0.30 wt % defoamer, 2.0 wt % zinc oxide, 4.0 wt % titanium dioxide, 25.0 wt % vinyl acrylic latex (55% solids), 2.70 wt % triaryl phosphate, 0.20 wt % PBC-40 (40% active), 0.30 wt % cellulosic thickener and 0.10 wt % biocide (in can stabilizer).

The resultant antimicrobial composition had a pH value of about 8.5 to about 9.5, a Brookfield viscosity of about 700 to about 900 cps and a solids content of about 23.0 wt % to about 27.0 wt %.

A sheeting article was prepared by impregnating a nonwoven porous Nylon sheeting material with the antimicrobial composition and drying the impregnated sheeting in an oven at about 180° F. for about 30 minutes.

The dried sheeting article was tested according to modified ASTM G 21 and the test results are listed in Table II.

Example 10

An antimicrobial composition and a sheeting article were prepared according to the procedure in Example 9, except that the antimicrobial composition was prepared by combining 37.15 wt % water, 0.30 wt % cellulosic thickener, 0.30 wt % anionic surfactant, 0.35 wt % defoamer, 2.8 wt % zinc oxide, 7.6 wt % titanium dioxide, 15.0 wt % alumina trihydrate, 7.10 wt % barium meta borate, 19.5 wt % ethylene vinyl acetate copolymer latex (50% solids), 5.30 wt % magnesium hydroxide, 0.20 wt % sodium omadine (40% active), 0.30 wt % IPBC-40 (40% active), 1.0 wt % propylene glycol, 0.40 wt % non-ionic surfactant and 2.70 wt % triaryl phosphate.

The resultant antimicrobial composition had a pH value of about 8.9 to about 9.9, a Brookfield viscosity of about 3,500 to about 5,500 cps and a solids content of about 49.0 wt % to about 53.0 wt %.

The dried sheeting article was tested according to modified ASTM G 21 and the test results are listed in Table II.

Example 11

An antimicrobial sheeting article was prepared by impregnating a porous brattice cloth substrate with the antimicrobial composition of Example 6 and drying the impregnated substrate in an oven at about 180° F. for about 30 minutes.

The dried sheeting article was tested according to modified ASTM G 21 and the test results are listed in Table II.

Example 12

An antimicrobial sheeting article was prepared by impregnating a porous woven fiberglass substrate with the antimicrobial composition of Example 10 and drying the impregnated sheeting substrate in an oven at about 180° F. for about 30 minutes.

The dried sheeting article was tested according to modified ASTM G 21 and the test results are listed in Table II.

Example 13

An antimicrobial sheeting article was prepared by impregnating a porous synthetic fiber blend substrate with the antimicrobial composition of Example 7 and drying the impregnated sheeting substrate in an oven at about 180° F. for about 30 minutes.

The dried sheeting article was tested according to modified ASTM G 21 and the test results are listed in Table II.

Example 14

An antimicrobial sheeting article was prepared by impregnating a porous synthetic fiber blend substrate with the antimicrobial composition of Example 10 and drying the impregnated sheeting substrate in an oven at about 180° F. for about 30 minutes.

The dried sheeting article was tested according to modified ASTM G 21 and the test results are listed in Table II.

Example 15

An antimicrobial sheeting article was prepared by impregnating a porous 10×10 fiberglass substrate with the antimicrobial composition of Example 3 and drying the impregnated sheeting substrate in an oven at about 180° F. for about 30 minutes.

The dried sheeting article was tested according to modified ASTM G 21 and the test results are listed in Table II.

Example 16

An antimicrobial sheeting article was prepared by impregnating a porous woven polyester substrate (70 U.S. mesh) with the antimicrobial composition of Example 8 and drying the impregnated sheeting substrate in an oven at about 180° F. for about 30 minutes.

The dried sheeting article was tested according to modified ASTM G 21 and the test results are listed in Table II.

TABLE II

| Examples | Sheeting substrates | Coating Coverage/gallon | Antimicrobial components(s) Gm/100 ft² | Rating* | Inhibiting growth Zone |
|---|---|---|---|---|---|
| Ex. 1 | Non-woven Nylon 1 oz/yd² | 130 ft² | 4.6 IPBC-40 | 0 | >10 mm |
| Ex. 2 | Non-woven Nylon 1 oz/yd² | 120 ft² | 5.0 IPBC-40<br>6.0 Zn Omadine | 0 | >10 mm |
| Ex. 3 | Non-woven Nylon 1 oz/yd² | 110 ft² | 5.7 IPBC-40<br>2.8 Na Omadine<br>71 ZnO | 0 | >10 mm |
| Ex. 4 | Non-woven FG 2 oz/yd² | 90 ft² | 6.8 IPBC-40<br>3.4 Na Omadine<br>85 ZnO | 0 | >10 mm |
| Ex. 5 | Non-woven FG 2 oz/yd² | 85 ft² | 5.6 IPBC-40<br>6.7 Zn Omadine<br>70 ZnO | 0 | >10 mm |
| Ex. 6 | Non-woven FG 2 oz/yd² | 80 ft² | 9.7 WBC-40<br>160 ZnO<br>880 ZB | 0 | 8 mm |
| Ex. 7 | Non-woven FG 2 oz/yd² | 70 ft² | 140 ZnO<br>770 ZB | 0 | 0 |
| Ex. 8 | Non-woven FG 2 oz/yd² | 65 ft² | 150 ZnO<br>740 BB | 0 | 0 |
| Ex. 9 | Non-woven FG 2 oz/yd² | 75 ft² | 4.2 IPBC-40<br>105 ZnO | 0 | 3 mm |
| Ex. 10 | Non-woven FG 2 oz/yd² | 65 ft² | 550 BB<br>5.2 Na Omadine<br>9.3 IPBC-40<br>220 ZnO | 0 | >10 mm |
| Ex. 11 | Brattice cloth 5 oz/yd² | 95 ft² | 6.4 IPBC-40<br>105 ZnO<br>580 ZB | 0 | 3 mm |
| Ex. 12 | Woven FG | 75 ft² | 485 BB<br>5.5 Na Omadine<br>8.2 IPBC-40<br>190 ZnO | 0 | >10 mm |
| Ex. 13 | Synthetic Fiber blend (6 oz/yd²) | 58 ft² | 170 ZnO<br>940 ZB | 0 | 0 |
| Ex. 14 | Synthetic Fiber blend (6 oz/yd²) | 75 ft² | 480 BB<br>5.4 Na Omadine<br>8.1 IPBC-40<br>190 ZnO | 0 | >10 mm |
| Ex. 15 | 10 × 10 FG | 50 ft² | 12.1 IPBC-40<br>6.0 Na Omadine<br>150 ZnO | 0 | 4 mm |
| Ex. 16 | Woven Polyester 70 U.S. mesh | 200 ft² | 250 BB<br>50 ZnO | 0 | 0 |

IPBC-40: iodo alkynyl alkyl carbamate ($C_4H_9NHCOOCH_2CCI$)
Na Omadine: Sodium Omadine ($C_5H_4NOSNa$)
Zn Omadine: Zinc Omadine ($C_{10}H_8N_2O_2S_2Zn$)
ZB: Zinc borate ($2ZnO \cdot 3B_2O_3 \cdot 5H_2O$)
BB: Barium meta borate ($BaB_2O_4 \cdot H_2O$)
FG: Fiberglass
*According to modified ASTM G-21

What is claimed is:

1. An antimicrobial article in a sheet form for constructions in industrial and commercial application, comprising a porous sheeting substrate impregnated with a water based antimicrobial composition, said water based antimicrobial composition comprising:
   a) at least one polymeric emulsion or dispersion;
   b) at least one substantially non-leaching antimicrobial component that is substantially free of environmentally hazardous material; and
   c) zinc oxide,
wherein said article exhibits zero growth of various fungus on either surfaces of said article according to modified ASTM G-21.

2. The antimicrobial article of claim 1 further comprising a layer of an adhesive disposed on at least one surface of said article.

3. The antimicrobial article of claim 2, wherein said adhesive comprises pressure sensitive adhesives, heat reactive adhesives or moisture curable adhesives.

4. The antimicrobial article of claim 2 further comprising a removable protective film attached on the exposed surface of said adhesive layer.

5. The antimicrobial article of claim 1, wherein said polymeric emulsion or dispersion has a glass transition temperature (Tg) of from about −70° F. (about −57° C.) to about 140° F. (about 60° C.).

6. The antimicrobial article of claim 1, wherein said antimircobial composition has a Brookfield viscosity of from about 1 cps to about 100,000 cps.

7. The antimicrobial article of claim 1, wherein said at least one antimicrobial component is chosen from sodium omadine, sodium borate, zinc omadine, zinc borate, calcium borate, barium metaborate, iodo alkynyl alkyl carbamates, diiodomethyl-p-tolylsulfone, 2-4-thiazolyl-benzimidaxole, 2-n-octyl-4-isothiazolin-3-one, zinc dimethyldithiocarbamate, zinc 2-mercaptobenzothiazole, potassium n-hydroxymethyl-n-methyldithiscarbamate, sodium 2-mercaptobenzothiazole, 5-hydroxyemthoxymethyl-1-aza-3,7-dioxa-bicyclooctane, 2,3,5,6-tetra-chloro-4-pyridine, zinc 2-pyridinethiol-1-oxide and N-trichloromethylthiophthalimide, tetrachloroisophthalonitrile, deltamethrin, fipronil, bifenthrin, chlorfenapyr, imidacloprid, and mixtures thereof.

8. The antimicrobial article of claim 7, wherein said antimicrobial component is chosen from zinc omadine, sodium omadine, iodo alkynyl alkyl carbamates, diiodomethylptolyl sulfone, zinc borate, barium metaborate, deltamethrin, and mixtures thereof.

9. The antimicrobial article of claim 1, wherein said porous sheeting substrate comprises woven or non-woven porous sheeting of fiberglass or other synthetics, Brattice cloth, cotton and other fabrics, heavy weight paper, light weight wire mesh, or ceramic cloths.

10. The antimicrobial article of claim 1, wherein said antimicrobial composition further comprises at least one pigment.

11. The antimicrobial article of claim 1, wherein said antimicrobial composition has a solids content of from about 10 wt % to about 77 wt %.

12. The antimicrobial article of claim 1, wherein said antimicrobial composition has a pH value of from about 3.0 to about 11.0.

13. A process of making the antimicrobial article of claim 1 comprising impregnating said porous sheeting substrate with said antimicrobial composition and drying said impregnated sheeting substrate.

14. The process of claim 1, further comprising applying a layer of an adhesive on at least one surface of said impregnated sheeting substrate.

15. The process of claim 1, further comprising applying a removable protective film on the exposed surface of said adhesive layer.

16. An antimicrobial adhesive article in a sheet form comprising
   i) a porous sheeting substrate impregnated with a water based antimicrobial composition, and
   ii) a layer of an adhesive disposed on at least one surface of said impregnated porous sheeting substrate,
wherein said water based antimicrobial composition comprising:
   a) at least one polymeric emulsion or dispersion; and
   b) at least one substantially non-leaching antimicrobial component that is substantially free of environmentally hazardous material.

17. The antimicrobial adhesive article of claim 16, further comprising a removable protective film attached on the exposed surface of said adhesive layer.

18. The antimicrobial adhesive article of claim 16, wherein said adhesive comprises pressure sensitive adhesives, heat reactive adhesives, or moisture curable adhesives.

19. The antimicrobial adhesive article of claim 16, wherein said polymeric emulsion or dispersion has a glass transition temperature (Tg) of from about −70° F. (about −57° C.) to about 140° F. (about 60° C.).

20. The antimicrobial adhesive article of claim 16, wherein said antimircobial composition has a Brookfield viscosity of from about 1 cps to about 100,000 cps.

21. The antimicrobial adhesive article of claim 16, wherein said at least one antimicrobial component is chosen from sodium omadine, sodium borate, zinc omadine, zinc borate, calcium borate, barium metaborate, iodo alkynyl alkyl carbamates, diiodomethyl-p-tolylsulfone, 2-4-thiazolyl-benzimidaxole, 2-n-octyl-4-isothiazolin-3-one, zinc dimethyldithiocarbamate, zinc 2-mercaptobenzothiazole, potassium n-hydroxymethyl-n-methyldithiscarbamate, sodium 2-mercaptobenzothiazole, 5-hydroxyemthoxymethyl-1-aza-3,7-dioxa-bicyclooctane, 2,3,5,6-tetra-chloro-4-pyridine, zinc 2-pyridinethiol-1-oxide and N-trichloromethylthiophthalimide, tetrachloroisophthalonitrile, deltamethrin, fipronil, bifenthrin, chlorfenapyr, imidacloprid, and mixtures thereof.

22. The antimicrobial adhesive article of claim 16, wherein said porous substrate comprises woven or non-woven porous sheeting of fiberglass or other synthetics, Brattice cloth, cotton and other fabrics, heavy weight paper, light weight wire mesh, or ceramic cloths.

23. The antimicrobial adhesive article of claim 16, wherein said antimicrobial composition further comprises zinc oxide.

24. The antimicrobial adhesive article of claim 16, wherein said antimicrobial composition further comprises at least one pigment.

25. The antimicrobial adhesive article of claim 16, wherein said adhesive layer includes at least one substantially non-leaching antimicrobial component that is substantially free of environmentally hazardous material.

26. The antimicrobial adhesive article of claim 16, wherein said antimicrobial composition has a solids content of from about 10 wt % to about 75 wt %.

27. The antimicrobial adhesive article of claim 16, wherein said antimicrobial composition has a pH value of from about 3.0 to about 11.0.

\* \* \* \* \*